(12) United States Patent
Kaine et al.

(10) Patent No.: US 8,712,107 B2
(45) Date of Patent: Apr. 29, 2014

(54) X-RAY IMAGING

(75) Inventors: Christopher James Kaine, Berkshire (GB); Alain Stephen Dekker, Surrey (GB)

(73) Assignee: Illinois Tool Works Inc., Glenview, IL (US)

( * ) Notice: Subject to any disclaimer, the term of this patent is extended or adjusted under 35 U.S.C. 154(b) by 901 days.

(21) Appl. No.: 12/600,247

(22) PCT Filed: May 13, 2008

(86) PCT No.: PCT/IB2008/001190
§ 371 (c)(1),
(2), (4) Date: Nov. 13, 2009

(87) PCT Pub. No.: WO2008/139316
PCT Pub. Date: Nov. 20, 2008

(65) Prior Publication Data
US 2010/0303304 A1    Dec. 2, 2010

(30) Foreign Application Priority Data
May 14, 2007    (GB) .................................. 0709183.8

(51) Int. Cl.
*G06K 9/00*    (2006.01)
(52) U.S. Cl.
USPC ........................................................ 382/110
(58) Field of Classification Search
None
See application file for complete search history.

(56) References Cited

U.S. PATENT DOCUMENTS

| | | | |
|---|---|---|---|
| 5,365,596 A | | 11/1994 | Dante et al. |
| 5,774,573 A | * | 6/1998 | Caspi et al. .................. 382/141 |
| 6,023,497 A | * | 2/2000 | Takahashi et al. ............. 378/57 |
| 6,687,395 B1 | | 2/2004 | Dietz et al. |
| 7,190,819 B2 | | 3/2007 | Viswanathan |
| 8,264,526 B2 | * | 9/2012 | Murali ............................ 348/47 |
| 2004/0161143 A1 | | 8/2004 | Dietz et al. |
| 2006/0251340 A1 | | 11/2006 | Karsenti |

FOREIGN PATENT DOCUMENTS

| | | |
|---|---|---|
| CN | 1343881 A | 4/2002 |
| CN | 1749740 A | 3/2006 |
| JP | 8145904 A | 6/1996 |
| WO | 0205547 A2 | 1/2002 |

OTHER PUBLICATIONS

PCT International Search Report and Written Opinion for PCT/IB2008/001190, dated Jun. 18, 2009.
Donghai Han etc., "Apply of Digital Image Processing for Foreign Body Detection in Agricultural Products and Carcass Products," Journal of Chinese Institute of Food Science and Technology, (z1), 2003.

* cited by examiner

*Primary Examiner* — Tahmina Ansari
(74) *Attorney, Agent, or Firm* — Fletcher Yoder P.C.

(57) ABSTRACT

An X-ray scanning apparatus for locating a contaminant in a product, the apparatus comprising: means for generating an X-ray image of the product; means for assigning a grey scale value to a plurality of pixels; means for identifying a plurality of suspect pixels; means, which for each suspect pixel: selects two neighboring pixels in a first direction lying on opposed sides of the suspect pixel and determines which of the first direction pixels has the lowest grey value; selects two neighboring pixels in a second direction lying on opposed sides of the suspect pixel and determines which of the second direction pixels has the lowest grey value; determines a first direction difference value by taking the grey value difference between the lowest grey value first direction pixel and the grey value of the suspect; determines a second direction difference value by taking the grey value difference between the lowest grey value second direction pixel and the grey value of the suspect; determines a first direction score from the first direction difference value; determines a second direction score from the second direction difference value; compares said scores with a threshold value; and identifies the suspect pixel as representing a contaminant if said threshold value is exceeded.

20 Claims, 2 Drawing Sheets

X-RAY IMAGING

CROSS-REFERENCE TO RELATED APPLICATIONS

This application claims priority to and the benefit of PCT Application No. PCT/IB2008/001190 entitled "X-Ray Imaging", filed on May 13, 2008, which is herein incorporated by reference in its entirety, and which claims priority to and the benefit of GB Application No. GB0709183.8, entitled "X-Ray Imaging", filed on May 14, 2007, which is herein incorporated by reference in its entirety.

This invention relates to X-ray imaging. In particular, it relates to an X-ray imaging means for identifying contaminants such as foreign bodies, for example metallic particles, in products, particularly foodstuffs.

BACKGROUND OF THE INVENTION

Generally, X-ray imaging identifies contaminants in products by a simple comparison of all the pixels in an image of the product against some value (or "threshold"). For example, every pixel in the image is assigned a grey value and these grey values are compared to a threshold grey value, wherein any pixels having a grey value lower than the threshold (dark pixels), are considered to represent contaminants. This technique may be adequate when the product is homogeneous, however, if the product is non-homogenous and contains light and dark regions, such as a bag of randomly arranged sweets, it is impossible to set a suitable threshold level. If the threshold level is set too high then bags not containing contaminants will trigger false alarms and have to be discarded. This is very costly as each then has to be carefully examined to determine whether it was a true or false alarm, for if the alarm is a true alarm then the source of the foreign particle may need to be established. This examination often has to take place immediately in case further action is required in the case of a true alarm signal.

More advanced imaging techniques are known, which involve looking at more localized changes in an image. Such techniques again involve assigning every pixel in the image a grey value. However, the grey value of each pixel is compared with an average grey value of pixels surrounding a pixel being considered. A threshold value is set and if the difference between the grey value of the pixel and the average grey value of the surrounding pixels is above the threshold, the pixel is deemed to represent a contaminant. This technique is more effective than the simple comparison technique, discussed above, but suffers similar drawbacks since there may be a great difference in grey values between an adjacent pixel bridging an edge of a product, resulting in false contaminant identification. This is particularly a problem with products of uneven shape, for example the bag of sweets, where the edge of the product cannot be predicted.

It is an object of the present invention to provide an improved means for identifying contaminants in a product, particularly foodstuffs, that is more effective with non-homogeneous and/or unevenly shaped products.

BRIEF SUMMARY OF THE INVENTION

According to a first aspect of the present invention, there is provided an X-ray scanning apparatus for locating a contaminant in a product, the apparatus comprising: means for generating an X-ray image of the product; means for assigning a grey scale value to a plurality of pixels; means for identifying a plurality of suspect pixels; means, which for each suspect pixel: selects two neighbouring pixels in a first direction lying on opposed sides of the suspect pixel and determines which of the first direction pixels has the lowest grey value; selects two neighbouring pixels in a second direction lying on opposed sides of the suspect pixel and determines which of the second direction pixels has the lowest grey value; determines a first direction difference value by taking the grey value difference between the lowest grey value first direction pixel and the grey value of the suspect; determines a second direction difference value by taking the grey value difference between the lowest grey value second direction pixel and the grey value of the suspect; determines a first direction score from the first direction difference value; determines a second direction score from the second direction difference value; compares said scores with a threshold value; and identifies the suspect pixel as representing a contaminant if said threshold value is exceeded.

It should be noted that an image may not exist in the sense that it is displayed, rather it may be generated and held within a computer, or similar, for processing without being displayed. The apparatus may however be provided with a screen on which the image is displayed. Furthermore, it should be noted that the neighbouring pixels need not be the pixels immediately adjacent the suspect pixel, rather they may be spaced from the suspect pixel by one or more intervening pixels. The neighbouring pixels may however be the pixels immediately adjacent the suspect pixel. The pixel spacing may be dependent on the contaminant particle size to be detected.

In an arrangement in accordance with the present invention, by determining the first and second direction scores on the basis of the neighbouring pixels having the lowest grey values, the pixels with the highest grey values (the lightest pixels) in both directions are ignored. This greatly reduces the chance of false triggering as a result of detecting an edge of a product or a free space (light) within a homogenous product, since the pixels in an image falling off the edge of a product or in a space within a homogeneous product would generally be those pixels having the highest grey values. A pixel within the image that falls off the edge of a product (i.e. a pixel in a portion of the image outside the product) is considered to have a grey value of 255 in the case of an 8-bit bitmap (the grey values of which range from 0 to 255) or a grey value of 65535 in the case of a 16-bit bitmap (the grey values of which range from 0 to 65535), etc.

Preferably, there is provided a means for weighting the first direction difference value in dependence on the grey value of the lowest grey value first direction pixel and weighting the second direction difference value in dependence on the grey value of the lowest grey value second direction pixel to determine the first and second direction scores. Most preferably, said weighting is performed in accordance with the equation: score=difference value×(1+(((maximum possible grey value+1)−lowest grey value)/(lowest grey value+1))). In the equation the maximum possible grey value is the highest possible grey value in the image (i.e. the grey value of the lightest possible pixel in the image—a white pixel). For example, in an 8-bit image this value is 255 and in a 16-bit image it is 65535.

By weighting the lowest difference values, small changes in dark regions (low grey values) of a homogeneous product are emphasised, which allows for detection of contaminants in dark regions of the associated image and reduces false triggering in lighter regions of the image. This weighting thus places the emphasis on darker objects which is advantageous in an image as most contaminants tend to cause dark spots on the image.

Preferably, the scores are individually compared with said threshold, with the suspect pixel being identified as representing a contaminant if one score exceeds the threshold value, if both scores exceed the threshold value, or if the average of the scores exceeds the threshold value.

By averaging the scores the suspect pixel is compared to its neighbours in both directions, which reduces false triggering. However, it may not always be appropriate to average the scores, for example, if the contaminants are very thin pieces of metal (such as needles) which may be vertically or horizontally aligned in the image. The measurement in one direction will be much larger than the measurement in the other direction and averaging the scores could result in sensitivity reduction for such contaminants.

Preferably, a pixel is identified as a suspect pixel if it has a grey value that exceeds a predetermined value.

By identifying suspect pixels on the basis of a predetermined value, the number of pixels unnecessarily compared to their neighbours is reduced, which increases the speed at which the apparatus may check a product for contaminants. The predetermined value may be set in accordance with the product being checked or the contaminants to be detected, where it is known that pixels having a grey value above the predetermined value cannot be contaminants. Preferably, a high predetermined value is selected, since this increases the chances of finding contaminants in lighter parts of the image. For very large images, the calculation for all pixels in the image may take more than 100 ms and it may be practical to use a lower threshold value in order to speed the calculation up.

Preferably, the first direction is orthogonal to the second direction.

Preferably, means are provided for setting a distance between each of the neighbouring pixels and the suspect pixel, in dependence on a user defined maximum contaminant size. Most preferably, each neighbouring pixel is spaced from the suspect pixel by such a distance that a contaminant of the maximum size may not span the suspect pixel and one of the neighbouring pixels.

By setting the distance between the suspect pixel and each of the neighbouring pixels to be such that a contaminant of maximum size may not span the suspect pixel and one of the neighbouring pixels it is ensured that any contaminant up to the user defined maximum contaminant size will be detected, since the contaminant will result in the suspect pixel (representative of the contaminant) having a low grey value relative to its neighbours, thereby providing a high difference value and high score. Were the contaminant to span the suspect pixel and a neighbouring pixel then both pixels would have low grey values but the difference value would be low, giving a low score, and the contaminant may avoid detection.

In order to enable the apparatus to detect both large and small contaminants in the same product, there may be multiple user defined maximum contaminant sizes input, such that for each suspect pixel the apparatus selects multiple pairs of neighbouring pixels in each direction, each pair selected being spaced a different distance in accordance with the multiple contaminant sizes. The neighbouring pixels spaced closer to the suspect pixel for smaller contaminants and further away for larger contaminants.

According to a further aspect of the present invention there is provided X-ray scanning method for locating a contaminant in a product, the method comprising the steps of: generating an X-ray image of the product; assigning a grey scale value to a plurality of pixels; identifying a plurality of suspect pixels; selecting two neighbouring pixels in a first direction lying on opposed sides of the suspect pixel and determining which of the first direction pixels has the lowest grey value; selecting two neighbouring pixels in a second direction lying on opposed sides of the suspect pixel and determining which of the second direction pixels has the lowest grey value; determining a first direction difference value by taking the grey value difference between the lowest grey value first direction pixel and the grey value of the suspect; determining a second direction difference value by taking the grey value difference between the lowest grey value second direction pixel and the grey value of the suspect; determining a first direction score from the first direction difference value; determining a second direction score from the second direction difference value; comparing said scores with a threshold value; and identifying the suspect pixel as representing a contaminant if said threshold value is exceeded.

BRIEF DESCRIPTION OF THE DRAWINGS

Embodiments of the invention will now be described, by way of example only, with reference to the accompanying drawings, in which.

DETAILED DESCRIPTION OF THE INVENTION

Figure 1:
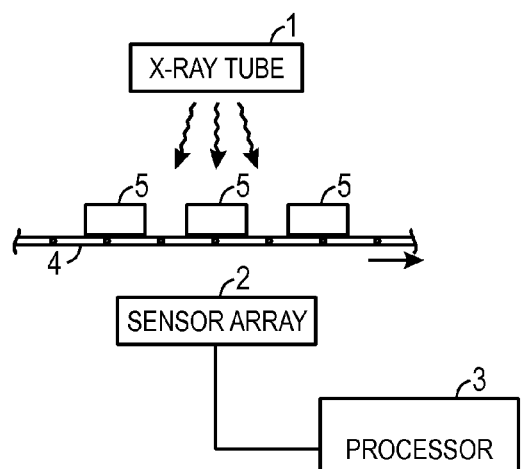
FIG. 1 schematically illustrates the X-ray imaging apparatus of the present invention.

Referring to FIG. 1, there is shown an X-ray imaging apparatus according to the present invention. The apparatus comprises an X-ray tube 1, a sensor array 2 for detecting contaminants and a computer 3 for processing the sensor data. A conveyer belt 4 is provided, along which products 5 to be scanned are conveyed. In use, a high voltage is applied to the X-ray tube, which emits a stream of X-rays that are focused and reduced to a fan beam that passes through a product on the conveyer belt before entering the sensor array 2, as is well known in the art. The sensor converts the X-ray signal into an 8-bit pixilated image. Each pixel has a grey value ranging from 0 to 255, where 0 represents black and 255 represents white. The image is passed to the computer for processing. There may or may not be a screen provided for displaying the image. The computer processes the 8-bit image using the following algorithm:

$X$=1 to Width(BITMAP)

$Y$=1 to Height(BITMAP)

Suspect=value($X,Y$)

UpDownMin=Minimum(Up,Down)

LeftRightMin=Minimum(Left,Right)

UpDownVal=UpDownMin−Suspect

LeftRightVal=LeftRightMin−Suspect

UpDownScore=UpDownVal*(1+(256−UpDownMin)/(UpDownMin+1))

LeftRightScore=LeftRightVal*(1+(256−LeftRightMin)/(LeftRightMin+1))

If UpDownScore>Slope Change then contaminant

If LeftRightScore>Slope Change then contaminant

The function of the algorithm will now be described in detail:

The algorithm firstly defines the pixel range (numbers the pixels) of the image and assigns a grey value to each pixel:

X=1 to Width(BITMAP)

Y=1 to Height(BITMAP)

The algorithm next identifies and selects a suspect pixel within the image, which has a grey value that exceeds a predetermined grey value:

Suspect=value(X,Y)

Whilst in the illustrated embodiment a predetermined grey value is specified to limit the number of pixels within the image that are compared to their neighbours so as to increase the speed at which the apparatus may check a product for contaminants, the predetermined grey value may be omitted in alternative arrangements, or set to a value of 255 so that the algorithm instead compares every pixel in the image to their neighbours.

Next, the algorithm selects a pair of neighbouring pixels in a vertical (first) direction that lie on opposed sides of the suspect pixel and determines which of the vertical pixels has the lowest grey value, and selects a pair of neighbouring pixels in a horizontal (second) direction that lie on opposed sides of the suspect pixel and determines which of the horizontal pixels has the lowest grey value:

UpDownMin=Minimum(Up,Down)

LeftRightMin=Minimum(Left,Right)

In accordance with a user defined maximum contaminant size, defined in accordance with the object being scanned and the likely contaminants to be detected, the algorithm selects a pair of neighbouring pixels in the vertical (UpDown) direction and a pair of neighbouring pixels in the horizontal (LeftRight) direction. The opposed neighbouring pixels in each of the vertical and horizontal directions are spaced from each other in accordance with the user defined maximum particle size so that a contaminant of maximum size may not span the suspect pixel and one of the neighbouring pixels. The neighbouring pixels will generally not be immediately adjacent the suspect pixel, although they can be if the contaminant to be detected is very small.

Whilst, in the illustrated embodiment the first and second directions are selected to be the horizontal and vertical directions, they may be any directions and the first and second directions do not need to be orthogonal to one another. They may for example, be arranged diagonally to each other.

Next, the algorithm determines a vertical (first) direction difference value by taking the grey value difference value between the lowest grey value vertical direction pixel and the grey value of the suspect, and determines a horizontal (second) direction difference value by taking the grey value difference value between the lowest grey value horizontal direction pixel and the grey value of the suspect:

UpDownVal=UpDownMin−Suspect

LeftRightVal=LeftRightMin−Suspect

The algorithm determines a vertical direction difference value by subtracting the grey value of the suspect from the lowest grey value vertical direction pixel, and determines a vertical direction difference value by subtracting the grey value of the suspect from the lowest grey value horizontal direction pixel.

Next, the algorithm determines a vertical (first) direction score by weighting the vertical direction difference value in dependence on the grey value of the lowest grey value vertical direction pixel, and determines a horizontal (second) direction score by weighting the horizontal direction difference value in dependence on the grey value of the lowest grey value horizontal direction pixel:

UpDownScore=UpDownVal*(1+(256−UpDownMin)/(UpDownMin+1))

LeftRightScore=LeftRightVal*(1+(256−LeftRightMin)/(LeftRightMin+1))

The algorithm determines the vertical (first) direction score by taking the vertical direction difference value and multiplying it by a sum. In the sum the vertical direction lowest grey value (i.e. the grey value of the lowest grey value vertical direction pixel) is deducted from the maximum possible grey value (255 in the present embodiment) to give a first value; the vertical direction lowest grey value is added to the minimum grey value (0) to give a second value; the first value is divided by the second value to give a third value; and an arbitrary value of 1 is added to the third value. An arbitrary value of 1 is also added to each of the maximum and minimum grey values (giving values of 256 and 1 respectively). The arbitrary values of 1 are added to avoid products of 0, which could give rise to a null value. The algorithm determines the horizontal (second) direction score in the same manner, using the relevant horizontal values. It should be noted that in alternative embodiments, in which the image is not an 8-bit image, the maximum possible grey value in the sum is substituted with the appropriate value. For example, in a 16-bit greyscale image the maximum possible grey value would be 65535.

Whilst, in the present embodiment the first and second direction scores are weighted, they need not be, the first direction score may be determined from the first direction difference value and the second direction score may be determined from the second direction difference value. However, by weighting the scores, small changes is dark regions of a homogeneous product are emphasised, which allows for detection of contaminants in dark regions of the associated image and reduces false triggering in lighter regions of the image.

Finally, the algorithm compares the vertical (first) direction score with a threshold, and compares the horizontal (second) direction score with the threshold, identifying the suspect pixel as a contaminant if the threshold value is exceeded:

If UpDownScore>Slope Change then contaminant

If LeftRightScore>Slope Change then contaminant

A threshold value (Slope Change) is set in accordance with the product being checked and the likely contaminants. The slope change is preferably set by passing a good (non-contaminated) product through the apparatus and analysing the image to determine the largest difference value between neighbouring pixels in the image. A threshold value input parameter is offset from this largest difference value by an amount that is dependent on how consistent the production process is (i.e. it is offset by a smaller amount for more tightly controlled processes and by a larger amount for more variable processes). A typical offset is around 15. For example, if the product was a homogenous product like a block of butter, then the largest difference value might be a value of 30, in which case the threshold value might be set to 45.

The algorithm compares the vertical and horizontal scores to the threshold value and if either the vertical score or the horizontal score exceeds the threshold value, i.e. the suspect pixel varies from its selected neighbouring pixels by more than this value, then the algorithm determines the suspect pixel to be representative of a contaminant within the product.

Whilst in the present embodiment the suspect pixel is identified as being representative of a contaminant if either of the vertical or horizontal scores exceeds the threshold, in an alternative arrangement the algorithm may require both of the scores to exceed the threshold. In a further alternative arrangement, the vertical and horizontal scores may be averaged, with the average score being compared to the threshold and the suspect pixel being identified as being representative of a contaminant if the average of the scores exceeds the threshold.

The computer runs the algorithm until every pixel in the image having a grey level that exceeds the predetermined value (or every pixel in the image assuming no predetermined value is set) has been processed.

A worked example in accordance with the present embodiment will now be described with reference to FIG. 2, which shows a raw 13×9 pixel image of a portion of a block of butter that contains a small contaminant (a 0.9 mm stainless steel fragment). A pure white (255) line has been added on the left of the image (column 1) in order to demonstrate how the apparatus of the present invention avoids edge detection. The contaminant (pixels (10,5) and (10,6) in the image) has been highlighted.

The settings for the algorithm in this example are:

Predetermined grey value=255, i.e. every pixel will be compared to it's neighbours, as may be seen in table 2;

Slope Change (threshold value)=35;

Filter Start=2, Filter End=2, i.e. the user defined maximum particle size is two pixels so that the neighbouring pixels are spaced from the suspect pixel by 2 pixels (there is an intervening pixel between the suspect and each of its neighbours); and Average is on, i.e. the average of the vertical and horizontal direction scores will be compared to the threshold.

TABLE 1

|   | 1 | 2 | 3 | 4 | 5 | 6 | 7 | 8 | 9 | 10 | 11 | 12 | 13 |
|---|---|---|---|---|---|---|---|---|---|----|----|----|----|
| 1 | 255 | 86 | 78 | 72 | 73 | 74 | 72 | 72 | 77 | 73 | 76 | 75 | 74 |
| 2 | 255 | 86 | 78 | 77 | 73 | 74 | 77 | 74 | 73 | 74 | 72 | 74 | 76 |
| 3 | 255 | 85 | 83 | 78 | 71 | 74 | 71 | 72 | 75 | 72 | 70 | 71 | 71 |
| 4 | 255 | 87 | 80 | 78 | 72 | 69 | 72 | 71 | 74 | 70 | 73 | 74 | 73 |
| 5 | 255 | 91 | 80 | 75 | 70 | 74 | 75 | 70 | 66 | 51 | 69 | 74 | 69 |
| 6 | 255 | 87 | 79 | 76 | 71 | 68 | 68 | 71 | 67 | 57 | 72 | 72 | 71 |
| 7 | 255 | 84 | 83 | 74 | 68 | 68 | 71 | 66 | 70 | 65 | 70 | 73 | 77 |
| 8 | 255 | 90 | 88 | 78 | 66 | 66 | 65 | 64 | 71 | 70 | 69 | 71 | 69 |
| 9 | 255 | 91 | 84 | 81 | 64 | 70 | 67 | 68 | 69 | 69 | 68 | 72 | 72 |

Figure 2:
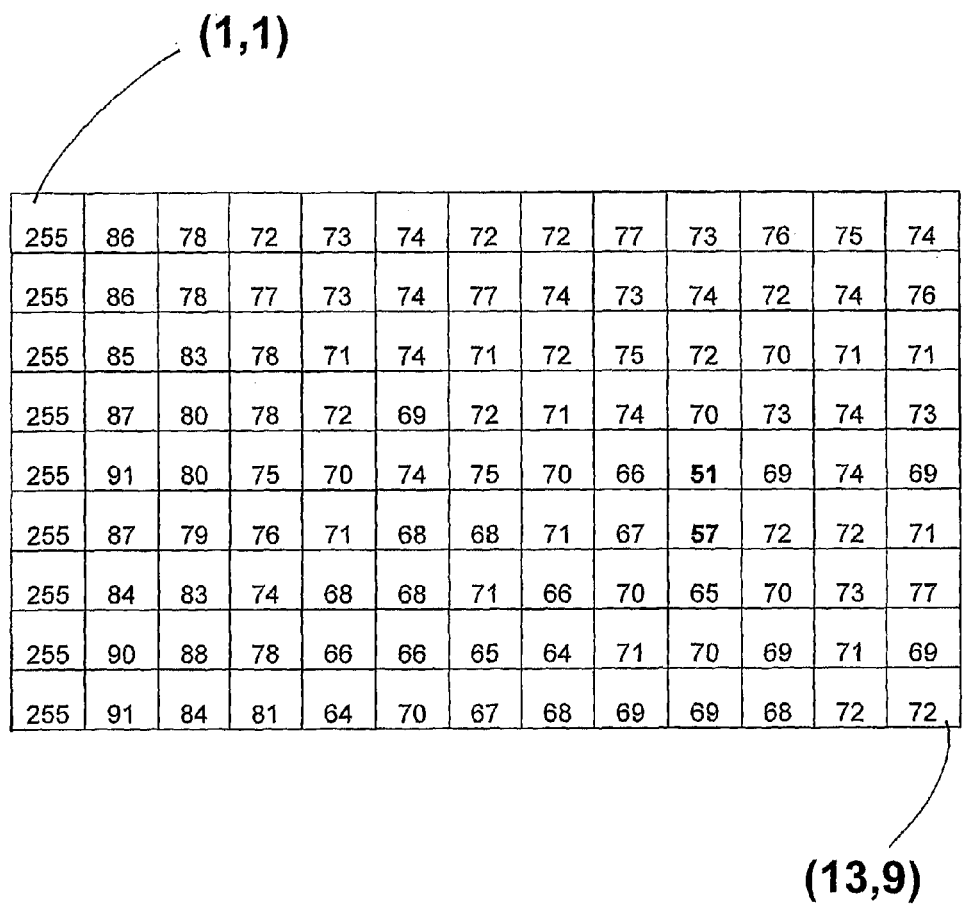
FIG. 2 illustrates the grey scale values that may be obtained from the X-ray detector array of the present invention when an edge of a product passes across the detector array.

Table 1 is populated with the grey values of the pixels in FIG. 2. The columns and rows of table 1 represent the columns and rows of the pixels within FIG. 2. As may be seen, the first column of pixels in FIG. 2 is white, representing a portion of the image falling off the butter (an edge of the butter), and the grey values of each of these pixels is 255 accordingly, as shown in table 1. Pixels (10, 5) and (10,6) within FIG. 2 represent the contaminant and these have corresponding low grey values of 51 and 57, as also shown in table 1.

TABLE 2

|   | 1 | 2 | 3 | 4 | 5 | 6 | 7 | 8 | 9 | 10 | 11 | 12 | 13 |
|---|---|---|---|---|---|---|---|---|---|----|----|----|----|
| 1 | −287 | −25 | 0 | 13 | −4 | −3 | 0 | 2 | −11 | −3 | −13 | −10 | −1 |
| 2 | −287 | −12 | −5 | −3 | 5 | −8 | −15 | −4 | 0 | −6 | 3 | 0 | −11 |
| 3 | −262 | −9 | −29 | −16 | −1 | −3 | 2 | −3 | −25 | −53 | 0 | 7 | −4 |
| 4 | −277 | −15 | −16 | −19 | −1 | 2 | −6 | −3 | −16 | −26 | −1 | −10 | −3 |
| 5 | −277 | −37 | −13 | −2 | 5 | −17 | −23 | −54 | 13 | 62 | −3 | −61 | 4 |
| 6 | −282 | −17 | −12 | −11 | −14 | 2 | −7 | −44 | 9 | 49 | −14 | −34 | −1 |
| 7 | −262 | −6 | −32 | −8 | −2 | 0 | −12 | 2 | −7 | −32 | −3 | −16 | −26 |
| 8 | −240 | −23 | −56 | −25 | 7 | 0 | 8 | 16 | −18 | −40 | 5 | 0 | 4 |
| 9 | −258 | −25 | −40 | −31 | 13 | −6 | 1 | −1 | −1 | −9 | 5 | −3 | 1 |

Table 2 is populated with the scores obtained by processing each pixel in FIG. 2 using the algorithm, with the settings described above, including a threshold value of 35. As may be seen by the scores in table 2, the pixels in the first column that represent the edge have not given rise to false triggering, since the scores in respect of the pixels adjacent to the first column all fall below the threshold of 35, whilst the contaminant has been detected, since the scores of the pixels, (10, 5) and (10,6), representing the contaminant are the only scores that exceed the threshold of 35.

In order to more clearly explain how these scores were arrived at, the algorithm is shown below, in respect of pixel (10,5) of FIG. 2 (as shown in table 1), which is representative of the contaminant:

UpDownMin=Minimum(72,65)=65

LeftRightMin=Minimum(70,74)=70

UpDownVal=UpDownMin−Suspect=65−51=14

LeftRightVal=LeftRightMin−Suspect=70−51=19

UpDownScore=14*(1+(256−65)/(65+1))=55

LeftRightScore=19*(1+(256−70)/(70+1))=69

Ave=(55+69)/2=62

62>35 so contaminant

In this example, as shown in FIG. 2, the contaminant is two pixels high in the vertical direction and spans pixels (10,5) and (10,6). When considering pixel (10,5), since the maximum particle size is set at two pixels, its immediately adjacent pixels, pixels (10,4) and (10,6) are not selected as neighbours. Were they to be selected then pixel (10,6) which has the lowest grey value (since the contaminant spans this pixel) would be compared to pixel (10,5), which would give rise to a low difference value and resulting score and would prevent detection of the contaminant in the vertical direction. However, since pixels (10,3) and (10,7) are selected as neighbours, by virtue of the user defined maximum particle setting, and the contaminant does not span these particles, there is a large difference value and the contaminant is detected in the vertical direction.

As demonstrated by this example, the present invention provides an X-ray imaging apparatus that is effective in locating contaminants within an article whilst avoiding false triggering as a result of edge detection or similar.

Whilst the embodiment and the example have considered an 8-bit greyscale image having grey values from 0 to 255 the algorithm may be applied to any alternative greyscale image, for example a 16-bit greyscale image having grey values from 0 to 65535. Furthermore, the algorithm could be extended to 24-bit colour images by considering each red, green and blue component as a separate 8-bit bitmap.

The invention claimed is:

1. An X-ray scanning apparatus for locating a contaminant in a product, the apparatus comprising:
   means for generating an X-ray image of the product;
   means for assigning a grey scale value to a plurality of pixels; means for identifying a plurality of suspect pixels, wherein a pixel of the plurality of pixels is identified as a suspect pixel if the pixel has a grey value that exceeds a predetermined grey value;
   means, which for each suspect pixel:
   selects two neighbouring pixels in a first direction lying on opposed sides of the suspect pixel and determines which of the first direction pixels has the lowest grey value;
   selects two neighbouring pixels in a second direction lying on opposed sides of the suspect pixel and determines which of the second direction pixels has the lowest grey value;
   determines a first direction difference value by taking the grey value difference between the lowest grey value first direction pixel and the grey value of the suspect pixel;
   determines a second direction difference value by taking the grey value difference between the lowest grey value second direction pixel and the grey value of the suspect pixel;
   determines a first direction score from the first direction difference value, wherein the first direction score is weighted based at least in part on the first direction difference value and a first ratio between the predetermined grey value and the lowest grey value of the first direction pixels;
   determines a second direction score from the second direction difference value, wherein the second direction score is weighted based at least in part on the second direction difference value and a second ratio between the predetermined grey value and the lowest grey value of the second direction pixels;
   compares said scores with a threshold value; and
   identifies the suspect pixel as representing a contaminant if said threshold value is exceeded.

2. The apparatus as claimed in claim 1, wherein the first ratio comprises the difference of the predetermined grey value and the lowest grey value of the first direction pixels over the lowest grey value of the first direction pixels, and the second ratio comprises the difference of the predetermined grey value and the lowest grey value of the second direction pixels over the lowest grey value of the second direction pixels.

3. The apparatus as claimed in claim 2, wherein said weighting is performed in accordance with the equation:

$$\text{score} = \text{difference value} \times (1 + (((\text{maximum possible grey value}+1) - \text{lowest grey value})/(\text{lowest grey value}+1))).$$

4. The apparatus as claimed in claim 3, wherein the scores are individually compared with said threshold.

5. The apparatus as claimed in claim 4, wherein the suspect pixel is identified as representing a contaminant if one score exceeds the threshold value.

6. The apparatus as claimed in claim 4, wherein the suspect pixel is identified as representing a contaminant if each score exceeds the threshold value.

7. The apparatus as claimed in claim 3, wherein the suspect pixel is identified as representing a contaminant if the average of the scores exceeds the threshold value.

8. The apparatus as claimed in any preceding claim, comprising means for setting a distance between each of the neighbouring pixels and the suspect pixel, in dependence on a user defined maximum contaminant size.

9. The apparatus as claimed in claim 8, wherein each neighbouring pixel is spaced from the suspect pixel by such a distance that a contaminant of the maximum size may not span the suspect pixel and one of the neighbouring pixels.

10. An X-ray scanning method for locating a contaminant in a product, the method comprising the steps of:
    generating an X-ray image of the product;
    assigning a grey scale value to a plurality of pixels; identifying a plurality of suspect pixels, wherein a pixel of the plurality of pixels is identified as a suspect pixel if the pixel has a grey value that exceeds a predetermined grey value;
    selecting two neighbouring pixels in a first direction lying on opposed sides of a suspect pixel and determining which of the first direction pixels has the lowest grey value;
    selecting two neighbouring pixels in a second direction lying on opposed sides of the selected suspect pixel and determining which of the second direction pixels has the lowest grey value;
    determining a first direction difference value by taking the grey value difference between the lowest grey value first direction pixel and the grey value of the suspect pixel;
    determining a second direction difference value by taking the grey value difference between the lowest grey value second direction pixel and the grey value of the suspect pixel;
    determining a first direction score from the first direction difference value, wherein the first direction score is weighted based at least in part on the first direction difference value and a first ratio between the predetermined grey value and the lowest grey value of the first direction pixels;
    determining a second direction score from the second direction difference value, wherein the second direction score is weighted based at least in part on the second direction difference value and a second ratio between the predetermined grey value and the lowest grey value of the second direction pixels;
    comparing said scores with a threshold value; and
    identifying the suspect pixel as representing a contaminant if said threshold value is exceeded.

11. A method as claimed in claim 10,
    wherein the first ratio comprises the difference of the predetermined grey value and the lowest grey value of the first direction pixels over the lowest grey value of the first direction pixels, and the second ratio comprises the difference of the predetermined grey value and the lowest grey value of the second direction pixels over the lowest grey value of the second direction pixels.

12. A method as claimed in claim 11, wherein said weighting is performed in accordance with the equation:

score difference value×(1+(((maximum possible grey value+1)−lowest grey value)/(lowest grey value+1))).

13. A method as claimed in claim 12, wherein the scores are individually compared with said threshold.

14. A method as claimed in claim 13, wherein the suspect pixel is identified as representing a contaminant if one score exceeds the threshold value.

15. A method as claimed in claim 13, wherein the suspect pixel is identified as representing a contaminant if each score exceeds the threshold value.

16. A method as claimed in claim 12, wherein the suspect pixel is identified as representing a contaminant if the average of the scores exceeds the threshold value.

17. A method as claimed in claim 16, wherein a pixel is identified as a suspect pixel if it has a grey value approximately equal to the highest possible grey value in the X-ray image.

18. A method as claimed in claim 17, wherein the first direction is orthogonal to the second direction.

19. A method as claimed any of claim 18, comprising the step of setting a distance between each of the neighbouring pixels and the suspect pixel, in dependence on a user defined maximum contaminant size.

20. A method as claimed in claim 19, wherein each neighbouring pixel is spaced from the suspect pixel by such a distance that a contaminant of the maximum size may not span the suspect pixel and one of the neighbouring pixels.

\* \* \* \* \*